United States Patent [19]

Suh et al.

[11] Patent Number: 5,348,988
[45] Date of Patent: Sep. 20, 1994

[54] DENTIN BONDING SYSTEM

[75] Inventors: Byoung Suh, Oak Brook; Martin Hamer, Skokie, both of Ill.

[73] Assignee: Bisco, Inc., Downers Grove, Ill.

[21] Appl. No.: 144,998

[22] Filed: Oct. 29, 1993

Related U.S. Application Data

[63] Continuation of Ser. No. 924,398, Aug. 3, 1992, abandoned, which is a continuation of Ser. No. 766,967, Sep. 26, 1991, abandoned, which is a continuation of Ser. No. 508,925, Apr. 12, 1990, abandoned.

[51] Int. Cl.$^5$ .............................. C08K 5/09
[52] U.S. Cl. ........................ 523/118; 106/35
[58] Field of Search .............. 106/35; 433/228.1; 523/113–118

[56] References Cited

U.S. PATENT DOCUMENTS 4,514,527 4/1985 Bowen .................................. 523/115

FOREIGN PATENT DOCUMENTS 1283554 11/1989 Japan .

*Primary Examiner*—Christine Skane
*Assistant Examiner*—Margaret Einsmann
*Attorney, Agent, or Firm*—Marshall, O'Toole, Gerstein, Murray & Borun

[57] ABSTRACT

Novel unsaturated carboxy esters for use in dentistry as bonding agents are produced by a reaction of unsaturated alcohols with cyclic acid dianhydrides. The dianhydrides which can be used in the invention are in general symmetrical compounds having an aromatic nucleus substituted with four carboxylic acid groups from which two moles of water have been removed to form two cyclic anhydride groupings. The unsaturated alcohols used for making the unsaturated carboxy esters have the formula $$H_2C=\overset{R}{\underset{|}{C}}-\overset{O}{\underset{\|}{(CO)}}_x-\overset{R_1}{\underset{|}{(CH)}}_n-OH$$

wherein R is H or CH$_3$,
R$_1$ is H, CH$_3$, or =CH$_2$,
n is an integer from 1 to 4 inclusive, and
x is 0 or 1.

5 Claims, No Drawings

DENTIN BONDING SYSTEM

This is a continuation of U.S. application Ser. No. 07/924,398, filed Aug. 3, 1992 now abandoned; in turn a continuation of Ser. No. 07/766,967 filed Sep. 26, 1991, now abandoned, in turn a continuation of Ser. No. 07/508,925 filed Apr. 12, 1990, now abandoned.

The present invention relates to a novel group of compounds useful as components in bonding systems for dental use, and to bonding systems incorporating such components which have superior adhesion to dentin and metal alloys used in dentistry.

BACKGROUND OF THE INVENTION

In our copending U.S. patent application Ser. No. 07/471,882, filed Jan. 29, 1990, now abandoned, the disclosure of which is expressly incorporated herein, we disclosed a novel group of compounds, which can be generally described as ethylenically unsaturated carboxy esters, which are effective dentin conditioners useful for treating the dentin of a tooth prior to use of a bonding resin and/or restorative composite. As disclosed in said application, the dentin conditioner causes a substantial increase in the strength of the bond between the dentin and the composite.

In accordance with the present invention, we have discovered a novel group of compounds to be used in conjunction with the dentin conditioner disclosed in our earlier application to further increase the bonding strength between dentin and a dental composite restorative material. In addition, the new compounds of the present invention can be used alone, i.e., without the dentin conditioners, to increase the bond strength between dental composites and metals used in dentistry for orthodontic brackets, metal frameworks in crowns and bridges, and the like.

BRIEF DESCRIPTION OF THE INVENTION

In accordance with the invention, there are provided novel unsaturated carboxy esters produced by a reaction of unsaturated alcohols with cyclic acid dianhydrides.

The dianhydrides which can be used in the invention are those having the formula

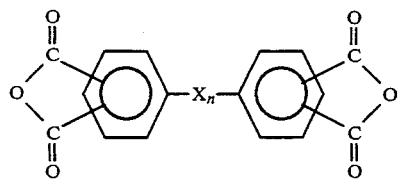

(I)

wherein X is

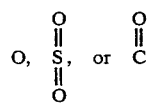

and
n is 0 or 1.

The unsaturated alcohols useful in the invention have the formula

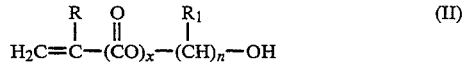

wherein R is H or CH$_3$,
R$_1$ is H, CH$_3$, or =CH$_2$,
n is an integer from 1 to 4 inclusive, and
x is 0 or 1.

The reaction product produced in this manner is used in accordance with the invention in conjunction with the dentin conditioner described in our copending application Ser. No. 07/471,882, and the reaction product of N-tolyl glycine or N-phenyl glycine with glycidyl methacrylate. These materials are applied in solution to an area in which a bond is desired, the bond being completed in the usual manner by use of a self-curing initiator or a light cure system.

DETAILED DESCRIPTION OF THE PREFERRED EMBODIMENTS

The dianhydrides useful in the invention are, in general, symmetrical compounds having an aromatic nucleus substituted with four carboxylic acid groups from which two moles of water have been removed to form two cyclic anhydride groupings. Representative of the anhydrides which can be used in the invention are those having the following structures:

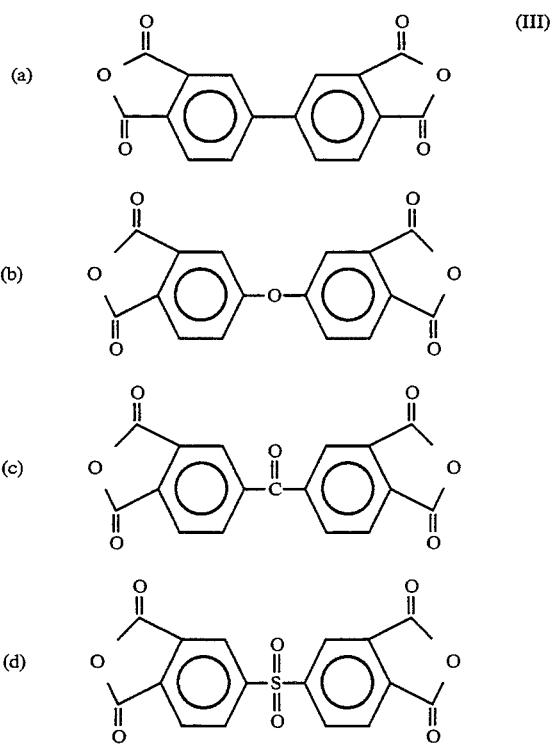

For producing the novel bonding agent components in accordance with the invention, the dianhydrides as described above are permitted to react in the presence of a small amount of a tertiary amine such as triethylamine, with preferably at least two molar equivalents of an unsaturated alcohol having the formula II.

The preferred unsaturated alcohols used in making the components of the invention are hydroxyethyl methacrylate and hydroxypropyl methacrylate. When these alcohols are reacted with suitable anhydrides in accordance with the invention, there is produced a group of preferred compounds having the formula

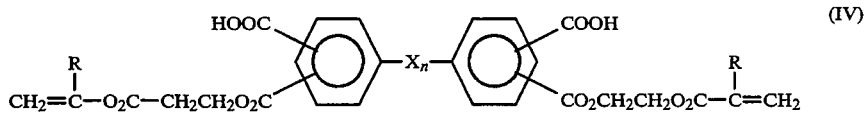

wherein R is H or CH₃,
X is

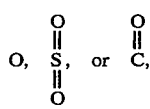

and
n is 0 or 1.

An example of the preparation of an unsaturated alcohol-dianhydride product is given in the following reaction, in which symmetrical biphenyl tetracarboxylic dianhydride is reacted with two moles of hydroxyethyl methacrylate.

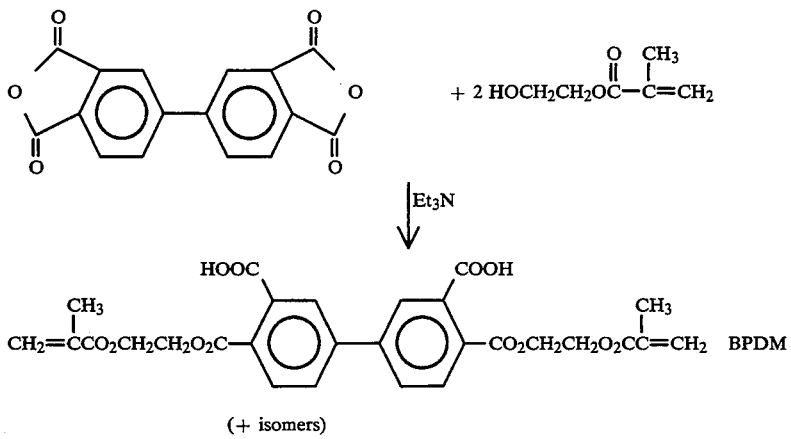

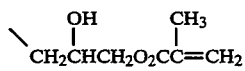

The product (BPDM) illustrated in the above reaction is one part of a novel dentin bonding system in accordance with the invention. The complete bonding system comprises (a) a dentin conditioner which is the reaction product of a cyclic acid anhydride having 3–12 carbon atoms with an ethylenically unsaturated alcohol having 3–12 carbon atoms, as disclosed in our copending application Ser. No. 07/471,882, now abandoned, and (b) a two-part dentin primer, the first part of which comprises the reaction product of an N-arylglycine with glycidyl methacrylate, having the formula $$\diagdown N\underset{\underset{\text{CH}_2\text{CHCH}_2\text{O}_2\text{CC}=\text{CH}_2}{|}}{\overset{\overset{\text{OH} \quad\quad \text{CH}_3}{|\quad\quad\quad|}}{}}$$

wherein R is hydrogen or CH₃.

When R is CH₃, the reaction product (V) is designated as NTG-GMA, and when R is H, as NPG-GMA.

The second part of the two-part dentin primer is selected from products, such as BPDM disclosed adore, prepared by reaction of a dianhydride of formula (I) with at least two moles of a hydroxyalkyl acrylate or methacrylate having formula (II).

The preparation of a typical second component of the dentin primer, e.g., BPDM, is illustrated in the following example.

EXAMPLE 1
PREPARATION OF BPDM

Symmetrical biphenyl tetracarboxylic dianhydride, 58.8 g (0.2 mole), was weighed into a flask. 2-Hydroxyethyl-methacrylate (HEMA), 78.1 g (0.6 mole) was added together with 5 ml of triethylamine. The mixture was stirred and heated at 80°–90° C. for one hour, during which time a clear solution resulted. At this time the infrared spectrum of the product revealed the disappearance of the anhydride absorption bands.

The superior effectiveness of the dentin bonding system of the invention for improving the bonding strength between dentin and a dental restorative material is illustrated by the data in Table 1 below. These data were obtained using extracted molars and premolars which were set in acrylic resin with a small section of clear plastic tubing as a mold. The cylindrical specimens were trimmed until a surface of dentin was sufficiently exposed, after which the exposed surface was polished with very fine grit sand paper.

A solution of a dentin conditioner, e.g., SA-HEMA, 20% in aqueous HEMA containing 40% water, was then brushed onto the prepared dentin surface for 30 seconds, and dried by a stream of compressed air for 5–10 seconds. The specimen surface was then treated with a mixture of equal parts of the primer components, e.g., NTG-GMA and BPDM, applying 3–4 coats of the mixture over the dried dentin conditioner. A coating of a commercial bonding agent (Bisfil dentin/enamel bonding agent) was applied to the dentin surface directly on top of the dried dentin primer.

Posts were made by partially filling No. 5 gel caps with a commercial light-cure dental composite material (Bisfil M) and curing under an appropriate radiation source. The remaining volume of the partially filled Gel caps was slightly overfilled with Bisfil M, and pressed against the cured bonding agent to eliminate air bubbles, and the excess composite was trimmed away. With the post held in place against the dentin surface, the composite material was light-cured for 60 seconds. The specimens were then placed in deionized water and held in a 37° C. oven for 24 hours. After that time, the specimens were removed, the gel caps having dissolved, and dried.

The bonds holding the posts to the dental surfaces were sheared off using an Instron universal testing instrument Model 11331. The tip of the blade of the instrument was adjusted to contact the cured post close to but not touching the specimen tooth surface. The shear force applied by the instrument was converted to $MN/m^2$, by dividing the shear force by the cross sectional area of the post.

TABLE I

| Sample No. | Dentin Conditioner | Dentin Primer Part 1 | Part 2 | Shear Bond (iii) $MN/m^2$ |
| --- | --- | --- | --- | --- |
| 1 | SA-HEMA (i) | NTG-GMA | PMDM (ii) | 12.0 |
| 2 | SA-HEMA | NTG-GMA | BPDM | 20.9 |
| 3 | SA-HEMA | NTG-GMA | ODDM (iv) | 16.4 |
| 4 | — | NTG-GMA | PMDM (ii) | 7.3 |
| 5 | — | NTG-GMA | BPDM | 12.1 |
| 6 | SA-HEMA | NTG-GMA | BTDM (v) | 17.0 |
| 7 | SBA-HEMA (vi) | NTG-GMA | PMDM | 13.4 |

(i) 20% solution of the reaction product of succinic anhydride with 2-hydroxyethyl methacrylate
(ii) commercial product from pyromellitic dianhydride + 2-hydroxyethyl methacrylate
(iii) average of 10 tests
(iv) 5% solution in acetone of the reaction product of Compound IIIb with excess HEMA
(v) 6% solution in acetone of the reaction product of Compound IIIc with excess HEMA
(vi) 10% solution in acetone of the reaction product of sulfobenzoic anhydride with excess HEMA The data of Table I illustrate the advantages of the bonding system of the invention. Bonds made using no dentin conditioner (Samples 4 and 5) or with a commercial product of the dentin primer (Samples 1 and 7) produced shear bond strengths less than 13.4 $MN/m^2$. By contrast, bonds made in accordance with the invention (Samples 2, 3 and 6) all produced bond strengths exceeding 17.0 $MN/m^2$.

The novel dianhydride-alcohol reaction products of the invention are also useful as metal primers for improving the bond between metal dental components and dental composites. The strength of such bonds is important in dentistry in those instances where metal is used in forming orthodontic brackets, metal frameworks in crowns and bridges, and the like.

For such usage, the dianhydride-alcohol product is applied in dilute solution (2–10%) in a suitable volatile solvent, such as acetone, to the metal surface. After evaporation of the solvent, the dental composite is applied to the metal surface in the usual manner.

Typical results of using the dianhydride-alcohol product of the invention in this manner are given in Table II. In the work reported in this table, the metal was Rexillium 3, a commercial product containing nickel (74–78%), chromium (12–14%), molybdenum (4–6%), and beryllium (1.8%). The metal surfaces were first wet sanded with fine (600 grit) sand paper, then sandblasted with 55 micron aluminum oxide. The primer under test was applied generally in two coats, after which a thin coat of a commercial self-cure opaquer (titanium dioxide in bis-GMA) was applied to render the metal invisible. Three types of opaquer can be used. One is a self-cure (two-component) opaquer in which the polymerization of the opaquer is initiated in a conventional manner by incorporating a free radical initiator such as a peroxide and an aromatic tertiary amine. Alternatively, a light cure opaquer (one component) can be used, in which there is incorporated a conventional photosensitizer such as anthraquinone or camphoroquinone. A third opaquer that can be used is a dual-cure opaquer. This is a two-component opaquer system formulated to cure by both light-cure and self-cure paths.

Reported in Table II are tests of bonding strength wherein posts of dental composite restorative material were cured against the metal surface and the shear strength determined as described above in connection with Table I. Included among the metal samples were those in which no primer was placed on the metal, as well as samples in which the dianhydride-alcohol product was used. In the Table, the primers identified as 4-META and Panavia-EX, were commercially-available materials represented as having the ability to improve the adherance of dental restorative materials to metal surfaces.

TABLE II

| Metal Primer[b] | Shear Bond Strength[a] psi | |
| --- | --- | --- |
| | Self-Cure Opaquer[c] | Light-Cure Opaquer |
| None | 1825 | 525 |
| PMDM[g] | 1257 | 645 |
| 4-META[d] | 2311 | 1428 |
| BPDM | 2829 (2904)[f] | 1578 (2898)[f] |
| ODDM | 1873 | — |
| DSDM[e] | 2695 (2682)[f] | 1549 (2809)[f] |
| Panavia EX[d] (Japan) | 1330 | — |

[a]Shear force required to break bond between composite opaquer and metal (Rexillium III) as measured with Instron instrument at 2 hours (37° C./Dry) after specimen preparation
[b]Applied to metal as a 4 to 10% solution in acetone
[c]Opaquer resin is used to block out appearance of metal
[d]Commercial product
[e]Dimethacrylate of dianhydride III(d)
[f]Dual-cured opaquer is used.
[g]Commercial product from pyromellitic dianhydride and 2-hydroxyethyl methacrylate.

It will be seen from the data of Table II that the primers of the present invention in general produce substantially higher bond strengths than did the commercially-available materials.

The foregoing detailed description has been given for clearness of understanding only, and no unnecessary limitations should be understood therefrom, as modifications will be obvious to those skilled in the art.

We claim:

1. A primer for improving the bond strength between a dental composite and dentin or a metal, sail primer comprising:
   (1) the reaction product of N-tolylglycine or N-phenylglycine with glycidyl methacrylate, and
   (2) a bonding agent comprising the reaction product of an ethylenically unsaturated alcohol having 3 to 12 carbon atoms with a cyclic anhydride having the formula

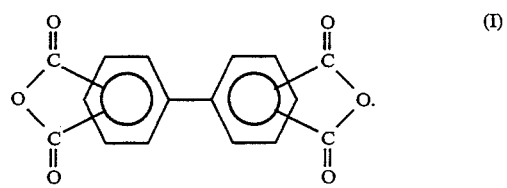
(I)

2. A primer in accordance with claim 1 wherein said alcohol is 2-hydroxyethyl methacrylate.

3. A primer in accordance with claim 1 wherein said bonding agent has the formula

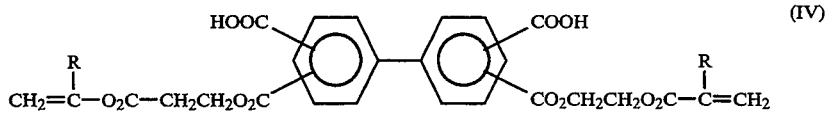

wherein R is H or CH$_3$.

4. A primer in accordance with claim 3 wherein R is CH$_3$.

5. A method for improving the bond strength between a dental composite and dentin or a metal which comprises applying to the surface of said dentin or said metal an effective quantity of a primer in accordance with claim 1 before the application of said dental composite thereto.

* * * * *

UNITED STATES PATENT AND TRADEMARK OFFICE
CERTIFICATE OF CORRECTION

PATENT NO. : 5,348,988

DATED : September 20, 1994

INVENTOR(S) : BYOUNG I. SUH ET AL.

It is certified that error appears in the above-identified patent and that said Letters Patent is hereby corrected as shown below:

Column 3, line 65, "adore" should be --above-- .

Column 4, line 65, "Gel" should be --gel-- .

Column 6, line 51, "sail" should be --said-- .

Signed and Sealed this

Twenty-first Day of March, 1995

Attest:

BRUCE LEHMAN

Attesting Officer

Commissioner of Patents and Trademarks